(12) United States Patent
Thapliyal et al.

(10) Patent No.: US 8,414,508 B2
(45) Date of Patent: Apr. 9, 2013

(54) SYSTEM AND METHOD FOR DELIVERY OF ENERGY TO TISSUE WHILE COMPENSATING FOR COLLATERAL TISSUE

(75) Inventors: Hira V. Thapliyal, Los Altos, CA (US); David A. Gallup, Alameda, CA (US); James W. Arenson, Woodside, CA (US)

(73) Assignee: VytronUS, Inc., Sunnyvale, CA (US)

( * ) Notice: Subject to any disclaimer, the term of this patent is extended or adjusted under 35 U.S.C. 154(b) by 481 days.

(21) Appl. No.: 12/609,274

(22) Filed: Oct. 30, 2009

(65) Prior Publication Data
US 2010/0113928 A1    May 6, 2010

Related U.S. Application Data

(60) Provisional application No. 61/109,881, filed on Oct. 30, 2008, provisional application No. 61/109,882, filed on Oct. 30, 2008.

(51) Int. Cl.
*A61B 17/00* (2006.01)
(52) U.S. Cl. .................................. 601/2; 604/22; 606/38
(58) Field of Classification Search .................. 600/407, 600/411, 412, 427, 438, 439, 474, 508, 549; 601/2; 604/22; 606/27–40; 607/2, 96–102, 607/115–132
See application file for complete search history.

(56) References Cited

U.S. PATENT DOCUMENTS

| | | | |
|---|---|---|---|
| 4,641,649 A | 2/1987 | Walinsky et al. |
| 4,757,820 A | 7/1988 | Itoh |
| 5,164,920 A | 11/1992 | Bast et al. |
| 5,246,438 A | 9/1993 | Langberg |
| 5,295,484 A | 3/1994 | Marcus et al. |
| 5,314,466 A | 5/1994 | Stern et al. |
| 5,405,346 A | 4/1995 | Grundy et al. |
| 5,471,988 A | 12/1995 | Fujio et al. |
| 5,718,241 A | 2/1998 | Ben-Haim et al. |

(Continued)

FOREIGN PATENT DOCUMENTS

| | | |
|---|---|---|
| DE | 10037660 | 2/2002 |
| WO | WO 99/02096 | 1/1999 |
| WO | WO 2005/117734 | 12/2005 |
| WO | WO 2006/034000 A1 | 3/2006 |

OTHER PUBLICATIONS

"A new treatment for atrial fibrillation?" Medical Device & Diagnostic Industry, Feb. 2006, p. 30; retrieved from the Internet: << http://www.devicelink.com/mddi/archive/06/02/013.html>>, 2 pages total.
Bushberg et al., *The Essential Physics of Medical Imaging*, 2nd edition, Lippincott Williams & Wilkins 2002, p. 491.

(Continued)

*Primary Examiner* — Parikha Mehta
(74) *Attorney, Agent, or Firm* — Wilson, Sonsini, Goodrich & Rosati

(57) ABSTRACT

A tissue ablation method for treating atrial fibrillation in a patient comprises locating an ostium of a pulmonary vein and positioning an interventional catheter adjacent the ostium. The interventional catheter has an energy source. Collateral tissue adjacent the ostium is located and tissue around the ostium is ablated with energy from the energy source so as to form a contiguous lesion circumscribing the ostium. The lesion blocks aberrant electrical pathways in the tissue so as to reduce or eliminate the atrial fibrillation. The ablating is modified so as to avoid ablating or otherwise damaging the collateral tissue.

26 Claims, 11 Drawing Sheets

U.S. PATENT DOCUMENTS

| | | |
|---|---|---|
| 5,735,811 A | 4/1998 | Brisken |
| 6,012,457 A | 1/2000 | Lesh |
| 6,024,740 A | 2/2000 | Lesh et al. |
| 6,052,576 A | 4/2000 | Lambourg |
| 6,064,902 A | 5/2000 | Haissaguerre et al. |
| 6,117,101 A | 9/2000 | Diederich et al. |
| 6,161,543 A | 12/2000 | Cox et al. |
| 6,164,283 A | 12/2000 | Lesh |
| 6,237,605 B1 | 5/2001 | Vaska et al. |
| 6,245,064 B1 | 6/2001 | Lesh et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,599 B1 | 7/2001 | Lesh et al. |
| 6,261,312 B1 | 7/2001 | Dobak, III et al. |
| 6,277,116 B1 | 8/2001 | Utely et al. |
| 6,305,378 B1 | 10/2001 | Lesh |
| 6,311,090 B1 | 10/2001 | Knowlton |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,379,378 B1 | 4/2002 | Werneth et al. |
| 6,383,151 B1 | 5/2002 | Diederich et al. |
| 6,387,089 B1 | 5/2002 | Kreindel et al. |
| 6,416,511 B1 | 7/2002 | Lesh et al. |
| 6,468,296 B1 | 10/2002 | Dobak, III et al. |
| 6,474,340 B1 | 11/2002 | Vaska et al. |
| 6,475,231 B2 | 11/2002 | Dobak, III et al. |
| 6,478,811 B1 | 11/2002 | Dobak, III et al. |
| 6,478,812 B2 | 11/2002 | Dobak, III et al. |
| 6,484,727 B1 | 11/2002 | Vaska et al. |
| 6,491,039 B1 | 12/2002 | Dobak, III |
| 6,491,716 B2 | 12/2002 | Dobak III et al. |
| 6,500,121 B1 | 12/2002 | Slayton et al. |
| 6,500,174 B1 | 12/2002 | Maguire et al. |
| 6,502,576 B1 | 1/2003 | Lesh |
| 6,514,244 B2 | 2/2003 | Pope et al. |
| 6,514,249 B1 | 2/2003 | Maguire et al. |
| 6,517,536 B2 | 2/2003 | Hooven et al. |
| 6,529,756 B1 | 3/2003 | Phan et al. |
| 6,533,804 B2 | 3/2003 | Dobak, III et al. |
| 6,540,771 B2 | 4/2003 | Dobak, III et al. |
| 6,542,781 B1 | 4/2003 | Koblish et al. |
| 6,546,935 B2 | 4/2003 | Hooven |
| 6,547,788 B1 | 4/2003 | Maguire et al. |
| 6,551,349 B2 | 4/2003 | Lasheras et al. |
| 6,576,001 B2 | 6/2003 | Werneth et al. |
| 6,585,752 B2 | 7/2003 | Dobak, III et al. |
| 6,592,576 B2 | 7/2003 | Andrews et al. |
| 6,595,989 B1 | 7/2003 | Schaer |
| 6,599,288 B2 | 7/2003 | Maguire et al. |
| 6,602,276 B2 | 8/2003 | Dobak, III et al. |
| 6,605,084 B2 | 8/2003 | Acker et al. |
| 6,607,502 B1 | 8/2003 | Maguire et al. |
| 6,607,527 B1 | 8/2003 | Ruiz et al. |
| 6,613,046 B1 | 9/2003 | Jenkins et al. |
| 6,635,054 B2 | 10/2003 | Fjield et al. |
| 6,645,199 B1 | 11/2003 | Jenkins et al. |
| 6,645,202 B1 | 11/2003 | Pless et al. |
| 6,648,908 B2 | 11/2003 | Dobak, III et al. |
| 6,652,515 B1 | 11/2003 | Maguire et al. |
| 6,652,517 B1 | 11/2003 | Hall et al. |
| 6,666,614 B2 | 12/2003 | Fechter et al. |
| 6,666,858 B2 | 12/2003 | Lafontaine |
| 6,669,655 B1 | 12/2003 | Acker et al. |
| 6,669,687 B1 | 12/2003 | Saadat |
| 6,676,688 B2 | 1/2004 | Dobak, III et al. |
| 6,676,689 B2 | 1/2004 | Dobak, III et al. |
| 6,676,690 B2 | 1/2004 | Werneth |
| 6,685,732 B2 | 2/2004 | Kramer |
| 6,689,128 B2 | 2/2004 | Sliwa, Jr. et al. |
| 6,692,488 B2 | 2/2004 | Dobak, III et al. |
| 6,695,873 B2 | 2/2004 | Dobak, III et al. |
| 6,701,931 B2 | 3/2004 | Sliwa, Jr. et al. |
| 6,702,842 B2 | 3/2004 | Dobak, III et al. |
| 6,711,444 B2 | 3/2004 | Koblish |
| 6,719,755 B2 | 4/2004 | Sliwa, Jr. et al. |
| 6,745,080 B2 | 6/2004 | Koblish |
| 6,752,805 B2 | 6/2004 | Maguire et al. |
| 6,758,847 B2 | 7/2004 | Maguire |
| 6,763,722 B2 | 7/2004 | Fjield et al. |
| 6,780,183 B2 | 8/2004 | Jimenez, Jr. et al. |
| 6,786,218 B2 | 9/2004 | Dobak, III |
| 6,805,128 B1 | 10/2004 | Pless et al. |
| 6,805,129 B1 | 10/2004 | Pless et al. |
| 6,814,733 B2 | 11/2004 | Schwartz et al. |
| 6,840,936 B2 | 1/2005 | Sliwa, Jr. et al. |
| 6,858,026 B2 | 2/2005 | Sliwa, Jr. et al. |
| 6,869,431 B2 | 3/2005 | Maguire et al. |
| 6,872,205 B2 | 3/2005 | Lesh et al. |
| 6,889,694 B2 | 5/2005 | Hooven |
| 6,893,438 B2 | 5/2005 | Hall et al. |
| 6,896,673 B2 | 5/2005 | Hooven |
| 6,899,710 B2 | 5/2005 | Hooven |
| 6,899,711 B2 | 5/2005 | Stewart et al. |
| 6,904,303 B2 | 6/2005 | Phan et al. |
| 6,905,494 B2 | 6/2005 | Yon et al. |
| 6,905,498 B2 | 6/2005 | Hooven |
| 6,905,509 B2 | 6/2005 | Dobak, III et al. |
| 6,908,464 B2 | 6/2005 | Jenkins et al. |
| 6,920,883 B2 | 7/2005 | Bessette et al. |
| 6,923,806 B2 | 8/2005 | Hooven et al. |
| 6,923,808 B2 | 8/2005 | Taimisto |
| 6,929,639 B2 | 8/2005 | Lafontaine |
| 6,932,811 B2 | 8/2005 | Hooven et al. |
| 6,949,095 B2 | 9/2005 | Vaska et al. |
| 6,949,097 B2 | 9/2005 | Stewart et al. |
| 6,953,460 B2 | 10/2005 | Maguire et al. |
| 6,954,977 B2 | 10/2005 | Maguire et al. |
| 6,955,173 B2 | 10/2005 | Lesh |
| 6,964,660 B2 | 11/2005 | Maguire et al. |
| 6,966,908 B2 | 11/2005 | Maguire et al. |
| 6,971,394 B2 | 12/2005 | Sliwa, Jr. et al. |
| 6,974,454 B2 | 12/2005 | Hooven |
| 6,984,233 B2 | 1/2006 | Hooven |
| 6,997,925 B2 | 2/2006 | Maguire et al. |
| 7,001,378 B2 | 2/2006 | Yon et al. |
| 7,001,415 B2 | 2/2006 | Hooven |
| 7,044,135 B2 | 5/2006 | Lesh |
| 7,063,682 B1 | 6/2006 | Whayne et al. |
| 7,142,905 B2 | 11/2006 | Slayton et al. |
| 7,275,450 B2 | 10/2007 | Hirai et al. |
| 7,285,116 B2 | 10/2007 | de la Rama et al. |
| 7,306,593 B2 | 12/2007 | Keidar et al. |
| 7,393,325 B2 | 7/2008 | Barthe et al. |
| 2002/0087151 A1 | 7/2002 | Mody et al. |
| 2003/0050630 A1 | 3/2003 | Mody et al. |
| 2003/0050631 A1 | 3/2003 | Mody et al. |
| 2005/0049582 A1 | 3/2005 | DeBenedictis et al. |
| 2005/0165388 A1 | 7/2005 | Bhola |
| 2005/0267453 A1 | 12/2005 | Wong et al. |
| 2006/0106375 A1* | 5/2006 | Werneth et al. .............. 606/32 |
| 2006/0122508 A1 | 6/2006 | Slayton et al. |
| 2007/0027445 A1 | 2/2007 | Gifford et al. |
| 2007/0066968 A1* | 3/2007 | Rahn .............................. 606/27 |
| 2007/0265609 A1 | 11/2007 | Thapliyal et al. |
| 2007/0265610 A1 | 11/2007 | Thapliyal et al. |
| 2008/039746 A1 | 2/2008 | Hissong et al. |
| 2008/0077200 A1 | 3/2008 | Bendett et al. |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0049099 A1 | 2/2010 | Thapliyal et al. |

OTHER PUBLICATIONS

Cox et al. "Current status of the Maze procedure for the treatment of atrial fibrillation," Semin Thorac Cardiovasc Surg. Jan. 2000;12(1):15-9.

Cox et al., "Electrophysiologic basis, surgical development, and clinical results of the maze procedure for atrial flutter and atrial fibrillation," Adv Card Surg. 1995;6:1-67.

Cox et al., "Modification of the maze procedure for atrial flutter and atrial fibrillation. II, Surgical technique of the maze III procedure," J Thorac Cardiovasc Surg. Aug. 1995;110(2):485-95.

Cox et al., "The development of the Maze procedure for the treatment of atrial fibrillation," Semin Thorac Cardiovasc Surg. Jan. 2000;12(1):2-14.

Gentry et al., "Integrated Catheter for 3-D Intracardiac Echocardiography and Ultrasound Ablation," IEEE Transactions on Ultrasonics, Ferroelectrics, and Frequency Control, vol. 51, No. 7, pp. 799-807, Jul. 2004.

Gill, "How to perform pulmonary vein isolation," Europace, 2004; 6 (2): 83-91; retrieved from the Internet: <<http://europace.oxfordjournals.org/cgi/reprint/6/2/83>>.

Gillinov et al., Atrial fibrillation: current surgical options and their assessment,: Annals of Thoracic Surgery 2002; 74:2210-7; retrieved from the Internet: <<http://ats.ctsnetjournals.org/cgi/reprint/74/6/2210>>.

Haissaguerre et al., "Spontaneous Initiation of Atrial Fibrillation by Ectopic Beats Originating in the Pulmonary Veins," New England J Med., Sep. 3, 1998; 339(10):659-666; retrieved from the Internet: <<http://content.nejm.org/cgi/reprint/339/10/659.pdf>>.

Levinson, "Endocardial Microwave Ablation: A New Surgical Approach for Atrial Fibrillation"; The Heart Surgery Forum, 2006.

Maessen et al., "Beating heart surgical treatment of atrial fibrillation with microwave ablation," Ann Thorac Surg 2002;74:S1307-S1311; retrieved from the Internet: <<http://ats.ctsnetjournals.org/cgi/reprint/74/4/S1307>>.

Nathan et al., "The junction between the left atrium and the pulmonary veins, An anatomic study of human hearts," Circulation 1966; 34:412-422; retrieved from the Internet: <<http://circ.ahajournals.org/cgi/reprint/34/3/412>>.

Sueda et al., "Efficacy of a simple left atrial procedure for chronic atrial fibrillation in mitral valve operations," Ann Thorac Surg 1997; 63:1070-1075.

Sueda et al., "Simple left atrial procedure for chronic atrial fibrillation associated with mitral valve disease," Ann Thorac Surg 1996; 62: 1796-1800.

Ter Haar, "Acoustic Surgery", Physics Today, 2001; 54(12):29-34.

U.S. Appl. No. 12/483,174, filed Jun. 11, 2009; first named inventor: Hira V. Thapliyal.

U.S. Appl. No. 13/630,727, filed Sep. 28, 2012, Thapliyal et al.

* cited by examiner

SYSTEM AND METHOD FOR DELIVERY OF ENERGY TO TISSUE WHILE COMPENSATING FOR COLLATERAL TISSUE

CROSS-REFERENCES TO RELATED APPLICATIONS

The present application is a non-provisional of, and claims the benefit of priority of U.S. Provisional Patent Application No. 61/109,881 filed Oct. 30, 2008 now expired; and 61/109,882 filed Oct. 30, 2008 now expired, the entire contents of which are incorporated herein by reference.

The present application is related to U.S. Provisional Patent Application Nos. 61/110,905 now expired; 61/115,403 now expired; 61/148,809 now expired; 61/109,973 now expired; 61/109,875 now expired; 61/109,879 now expired; 61/109,889 now expired; 61/109,893 now expired; 61/254,997 now expired; and U.S. patent application Ser. Nos. 11/747,862 (now U.S. Pat. No. 7,950,397); 11/747,867 (now U.S. Pat. No. 7,942,871); 12/480,929 now pending US Pub. No. 2009/0312755); 12/480,256 (now abandoned US Pub. No. 2009/0312693); 12/483,174 (now abandoned US Pub. No. 2010/0152582); 12/482,640 (now pending US Pub. No. 2009/0312673); 12/505,326 (now pending US Pub. No. 2010/0049099); and 12/505,335 (now pending US Pub. No. 2010/0016762); the entire contents of which are incorporated herein by reference.

BACKGROUND OF THE INVENTION

1. Field of the Invention

The present application generally relates to systems and methods for creating ablation zones in human tissue. More specifically, the present application relates to the treatment of atrial fibrillation of the heart by using ultrasound energy, and even more specifically, the present application relates to ablation systems and methods used to treat atrial fibrillation that detect and compensate for collateral tissue such as the phrenic nerve, esophagus, and other tissue.

The condition of atrial fibrillation (AF) is characterized by the abnormal (usually very rapid) beating of the left atrium of the heart which is out of synch with the normal synchronous movement ('normal sinus rhythm') of the heart muscle. In normal sinus rhythm, the electrical impulses originate in the sino-atrial node ('SA node') which resides in the right atrium. The abnormal beating of the atrial heart muscle is known as 'fibrillation' and is caused by electrical impulses originating instead at points other than the SA node, for example, in the pulmonary veins (PV).

There are pharmacological treatments for this condition with varying degree of success. In addition, there are surgical interventions aimed at removing the aberrant electrical pathways from PV to the left atrium ('LA') such as the 'Cox-Maze III Procedure'. This procedure has been shown to be 99% effective but requires special surgical skills and is time consuming. Thus, there has been considerable effort to copy the Cox-Maze procedure using a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ('RF') electrical energy to heat the muscle tissue and thereby ablate it. The aberrant electrical impulses are then prevented from traveling from PV to the atrium (achieving the 'conduction block') and thus avoiding the fibrillation of the atrial muscle. Other energy sources, such as microwave, laser, and ultrasound have been utilized to achieve the conduction block. In addition, techniques such as cryoablation, administration of ethanol, and the like have also been used.

More recent approaches for the treatment of AF involve the use of ultrasound energy. The target tissue of the region surrounding the pulmonary vein is heated with ultrasound energy emitted by one or more ultrasound transducers.

When delivering energy to tissue, in particular when ablating tissue with ultrasound to treat atrial-fibrillation, a transmural lesion (burning all the way through the tissue) must be made to form a proper conduction block. Achieving a transmural lesion though has many challenges. Health complications may arise when esophageal or other collateral tissue such as the phrenic nerve is ablated. Thus there is a need in the medical device field to provide an ablation system and method of use that detects and compensates for collateral tissue during the ablation process. It would also be desirable to provide an ablation system that is easy to use, easy to manufacture and that is lower in cost than current commercial systems.

2. Description of Background Art

Patents related to the treatment of atrial fibrillation include, but are not limited to the following: U.S. Pat. Nos. 6,997,925; 6,996,908; 6,966,908; 6,964,660; 6,955,173; 6,954,977; 6,953,460; 6,949,097; 6,929,639; 6,872,205; 6,814,733; 6,780,183; 6,666,858; 6,652,515; 6,635,054; 6,605,084; 6,547,788; 6,514,249; 6,502,576; 6,416,511; 6,383,151; 6,305,378; 6,254,599; 6,245,064; 6,164,283; 6,161,543; 6,117,101; 6,064,902; 6,052,576; 6,024,740; 6,012,457; 5,405,346; 5,314,466; 5,295,484; 5,246,438; and 4,641,649.

Patent Publications related to the treatment of atrial fibrillation include, but are not limited to International PCT Publication No. WO 99/02096; and U.S. Patent Publication No. 2005/0267453.

Scientific publications related to the treatment of atrial fibrillation include, but are not limited to: Haissaguerre, M. et al., *Spontaneous Initiation of Atrial Fibrillation by Ectopic Beats Originating in the Pulmonary Veins*, New England J Med., Vol. 339:659-666; J. L. Cox et al., *The Development of the Maze Procedure for the Treatment of Atrial Fibrillation*, Seminars in Thoracic & Cardiovascular Surgery, 2000; 12: 2-14; J. L. Cox et al., *Electrophysiologic Basis, Surgical Development, and Clinical Results of the Maze Procedure for Atrial Flutter and Atrial Fibrillation*, Advances in Cardiac Surgery, 1995; 6: 1-67; J. L. Cox et al., *Modification of the Maze Procedure for Atrial Flutter and Atrial Fibrillation. II, Surgical Technique of the Maze III Procedure*, Journal of Thoracic & Cardiovascular Surgery, 1995; 110:485-95; J. L. Cox, N. Ad, T. Palazzo, et al. *Current Status of the Maze Procedure for the Treatment of Atrial Fibrillation*, Seminars in Thoracic & Cardiovascular Surgery, 2000; 12: 15-19; M. Levinson, *Endocardial Microwave Ablation: A New Surgical Approach for Atrial Fibrillation*; The Heart Surgery Forum, 2006; Maessen et al., *Beating Heart Surgical Treatment of Atrial Fibrillation with Microwave Ablation*, Ann Thorac Surg 74: 1160-8, 2002; A. M. Gillinov, E. H. Blackstone and P. M. McCarthy, *Atrial Fibrillation: Current Surgical Options and their Assessment*, Annals of Thoracic Surgery 2002; 74:2210-7; Sueda T., Nagata H., Orihashi K., et al., *Efficacy of a Simple Left Atrial Procedure for Chronic Atrial Fibrillation in Mitral Valve Operations*, Ann Thorac Surg 1997; 63:1070-1075; Sueda T., Nagata H., Shikata H., et al.; *Simple Left Atrial Procedure for Chronic Atrial Fibrillation Associated with Mitral Valve Disease*, Ann Thorac Surg 1996; 62:1796-1800; Nathan H., Eliakim M., *The Junction Between the Left Atrium and the Pulmonary Veins, An Anatomic Study*

*of Human Hearts*, Circulation 1966; 34:412-422; Cox J. L., Schuessler R. B., Boineau J. P., *The Development of the Maze Procedure for the Treatment of Atrial Fibrillation*, Semin Thorac Cardiovasc Surg 2000; 12:2-14; and Gentry et al., *Integrated Catheter for 3-D Intracardiac Echocardiography and Ultrasound Ablation*, IEEE Transactions on Ultrasonics, Ferroelectrics, and Frequency Control, Vol. 51, No. 7, pp 799-807.

BRIEF SUMMARY OF THE INVENTION

The present application generally relates to systems and methods for creating ablation zones in human tissue. More specifically, the present application relates to the treatment of atrial fibrillation of the heart by using ultrasound energy, and even more specifically, the present application relates to ablation systems and methods used to treat atrial fibrillation that detect and compensate for collateral tissue such as the esophagus, phrenic nerve, and other tissue.

In a first aspect of the present invention a tissue ablation method for treating atrial fibrillation in a patient comprises locating an ostium of a pulmonary vein, and positioning an interventional catheter adjacent the ostium. The interventional catheter has an energy source. Collateral tissue adjacent the ostium is identified and tissue around the ostium is transmurally ablated with energy from the energy source. This forms a contiguous transmural lesion circumscribing the ostium and the lesion blocks aberrant electrical pathways in the tissue so as to reduce or eliminate the atrial fibrillation. The ablating is modified so as to avoid ablating or otherwise damaging the collateral tissue.

The interventional catheter may further comprise a sensor adjacent the energy source. The locating step may comprise delivering energy from the energy source toward the tissue adjacent the ostium, and sensing energy reflected from the tissue adjacent the ostium with the sensor. The sensor may comprise at least a portion of the energy source.

The positioning step may comprise intravascularly advancing the interventional catheter into a left atrium of the patient's heart. Identifying may comprise characterizing properties of the tissue adjacent the ostium and comparing the properties with known tissue properties. Identifying may be a part of a diagnostic sweep of tissue adjacent the ostium. The sweep may be a systematic scan to acquire information about the tissue adjacent the ostium. The identifying step may be performed while the ablating step is performed.

The modifying may comprise modifying the transmural lesion so as to avoid the collateral tissue. Modifying may comprise changing an originally planned transmural lesion path to a new transmural lesion path or modifying may comprise changing the energy emitted from the energy source so as to avoid damaging the collateral tissue.

The collateral tissue may comprise an esophagus. Identifying the esophagus may comprise positioning an esophageal detection device into the esophagus. Identifying may also comprise sensing the presence of the detection device through one or more layers of tissue. The esophageal detection device may comprise a balloon catheter which may be filled with a fluid such as saline, water, gas (e.g. carbon dioxide, air). Liquids such as saline or water are preferably filled with microbubbles to enhance echogenicity. The method may further comprise sensing water in the balloon catheter with an ultrasound signal delivered by the energy source. The esophageal detection device may also comprise a transponder such as a reflective material, a chemical substance, RFID tag, a capacitive plate, an inductive component, an ultrasound transducer, and an infrared light. The esophageal detection device may further protect the esophagus by cooling the esophagus. Identifying the esophagus may comprise sensing the esophageal detection device with the interventional catheter.

The collateral tissue may also comprise a phrenic nerve. Identifying the nerve may comprise applying pressure or an electrical signal to the phrenic nerve and monitoring the patient for a reflex response. The reflex response may comprise a hiccup. Monitoring may comprise audibly monitoring the patient. Applying pressure may comprise directing an ultrasound pressure wave to the phrenic nerve, pushing on the nerve with an instrument or electrically stimulating the nerve.

In another aspect of the present invention, a tissue ablation system for treating atrial fibrillation in a patient comprises an interventional catheter having an energy source and a sensor. The energy source is adapted to deliver a beam of energy to tissue thereby ablating tissue around an ostium of a pulmonary vein to form a contiguous lesion circumscribing the ostium. The contiguous lesion blocks aberrant electrical pathways in the tissue so as to reduce or eliminate the atrial fibrillation. The system also includes an esophageal detection device positionable in the esophagus. The detection device has a transponder detectable by the sensor through one or more layers of tissue.

The detection device may comprise a balloon catheter and the balloon catheter may be at least partially filled with a fluid such as saline, water, gas (e.g. carbon dioxide, air). Liquids such as saline or water are preferably filled with microbubbles to enhance echogenicity. The beam of energy may comprise an ultrasound signal that reflects off the saline or water filled portion of the balloon catheter and is sensed by the sensor. The transponder may comprise one of a reflective material, a chemical substance, RFID tag, a capacitive plate, an inductive component, an ultrasound transducer and an infrared light. The energy source may comprise an ultrasound transducer, and the sensor may comprise at least a portion of the ultrasound transducer.

These and other embodiments are described in further detail in the following description related to the appended drawing figures.

DETAILED DESCRIPTION OF THE INVENTION

The following description of the preferred embodiments of the invention is not intended to limit the invention to these preferred embodiments, but rather to enable any person skilled in the art to make and use this invention.

Figure 1:
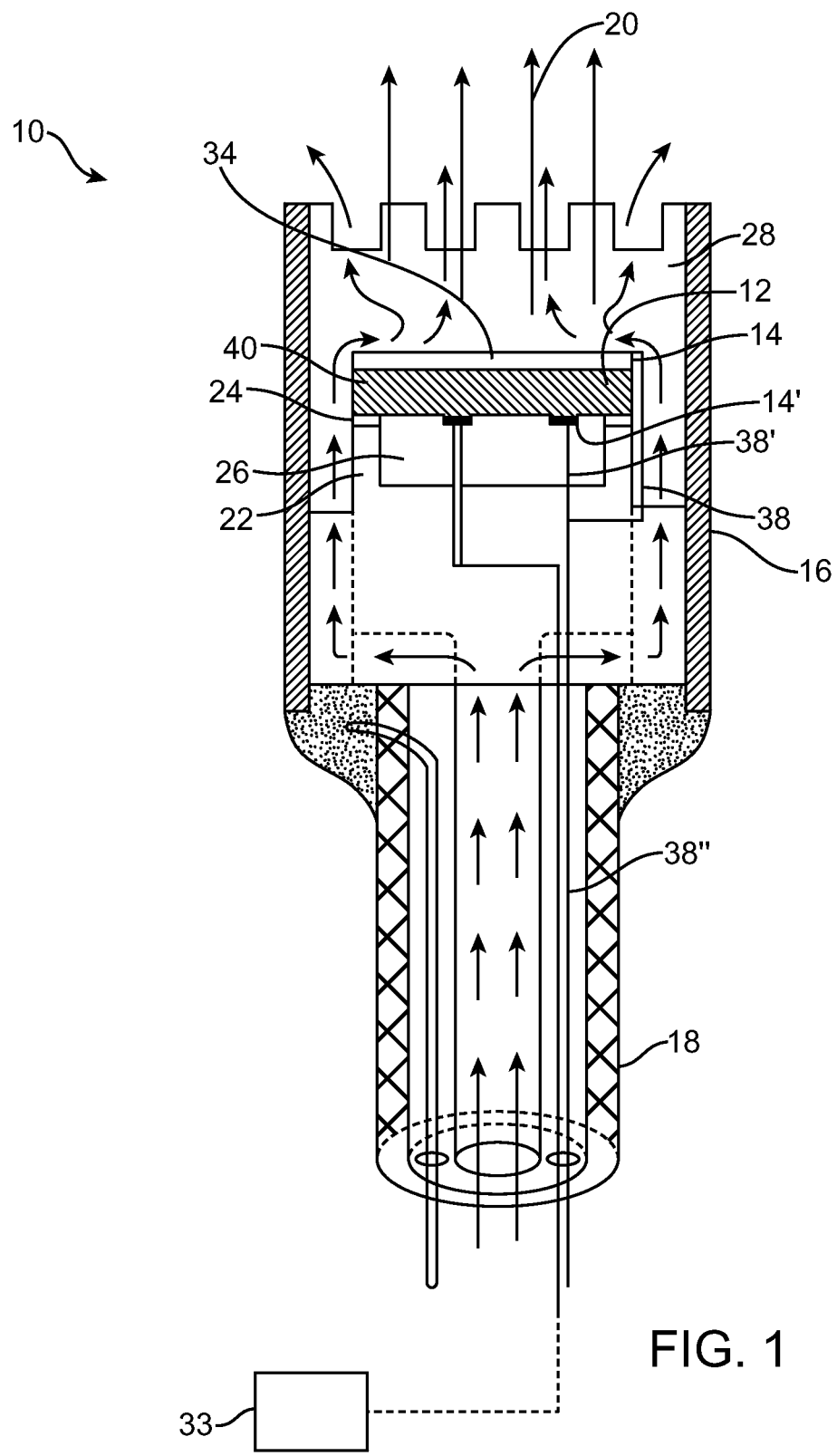
FIG. 1 illustrates an exemplary embodiment of an energy delivery device.

As shown in FIG. 1, the energy delivery system 10 of the preferred embodiments includes an energy source 12, that functions to provide a source of ablation energy, and an electrical attachment 14, coupled to the energy source 12, that functions to energize the energy source 12 such that it emits an energy beam 20. The energy delivery system 10 of the preferred embodiments also includes a sensor 40 or the energy source 12 may also serve as the sensor to detect the gap (distance of the tissue surface from the energy source 12), the thickness of the tissue targeted for ablation, the characteristics of the ablated tissue, and any other suitable parameter or characteristic of the tissue and/or the environment around the energy delivery system 10. The energy delivery system 10 of the preferred embodiments also includes a processor 33 operatively coupled to the sensor and to the electrical attachment 14, that controls the electrical attachment 14 and/or the electrical signal delivered to the energy source 12 based on the information from the sensor 40. The energy delivery system 10 is preferably designed for delivering energy to tissue, more specifically, for delivering ablation energy to tissue, such as heart tissue, to create a conduction block—isolation and/or block of conduction pathways of abnormal electrical activity, which typically originate from the pulmonary veins in the left atrium—for treatment of atrial fibrillation in a patient. The system 10, however, may be alternatively used with any suitable tissue in any suitable environment and for any suitable reason.

1. The Energy Source. As shown in FIG. 1, the energy source 12 of the preferred embodiments functions to provide a source of ablation energy and emit an energy beam 20. The energy source 12 is preferably moved and positioned within a patient, preferably within the left atrium of the heart of the patient, such that the energy source 12 is positioned at an appropriate angle with respect to the target tissue. The angle is preferably any suitable angle such that the emitted energy beam 20 propagates into the target tissue, and preferably generates a transmural lesion (i.e. a lesion through the thickness of the tissue that preferably creates a conduction block, as described below). Angles between 40 and 140 degrees are preferable because in this range the majority of the energy beam will preferably propagate into the tissue and the lesion depth needed to achieve transmurality is preferably minimally increased from the ideal orthogonal angle.

Figure 2:
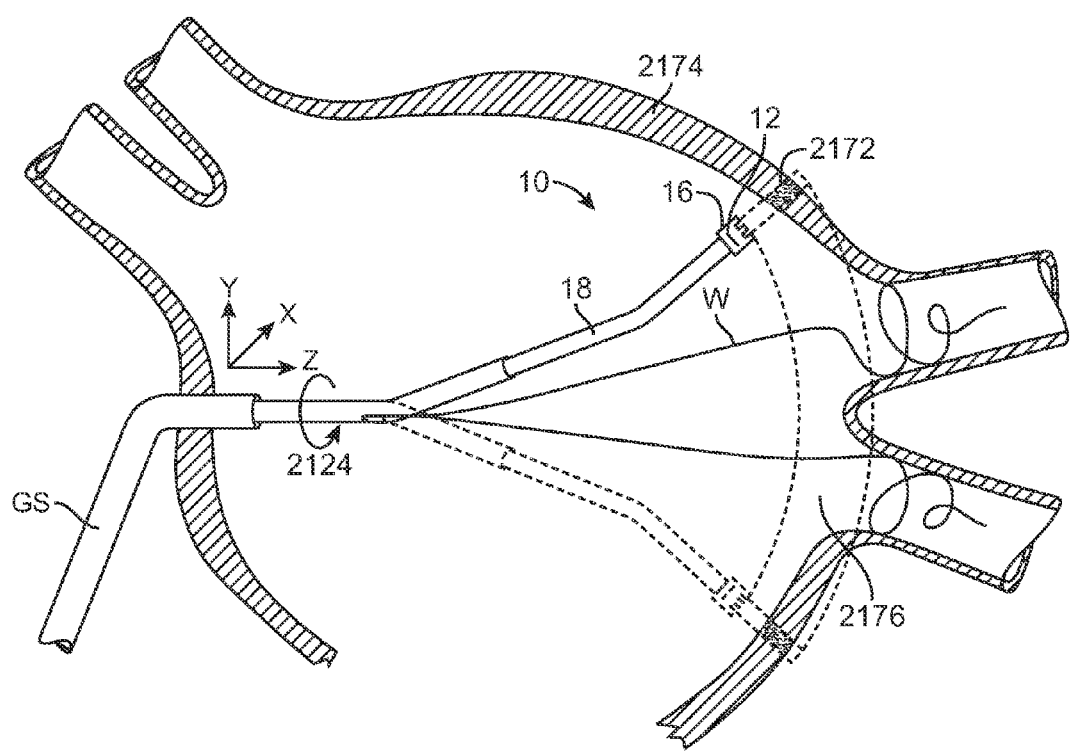
FIG. 2 illustrates exemplary use of the energy delivery device in FIG. 1 to ablate cardiac tissue.

As shown in FIG. 1, the energy source 12 is preferably coupled to a housing 16. The energy source 12 and the housing 16 are preferably positionable within the patient. For example, the housing 16, and the energy source 12 within it, are preferably moved to within the left atrium of the heart (or in any other suitable location) and, once positioned there, are preferably moved to direct the energy source 12 and the emitted energy beam 20 towards the target tissue at an appropriate angle. Furthermore, the housing 16, and the energy source 12 within it, are preferably moved along an ablation path such that the energy source 12 provides a partial or complete zone of ablation along the ablation path. The zone of ablation along the ablation path preferably has any suitable geometry to provide therapy, such as providing a conduction block for treatment of atrial fibrillation in a patient. The zone of ablation along the ablation path may alternatively provide any other suitable therapy for a patient. A linear ablation path is preferably created by moving the housing 16, and the energy source 12 within it, along an X, Y, and/or Z-axis. As shown in FIG. 2, the motion of the distal portion of the elongate member 18 in and out of the guide sheath portion GS of the elongate member 18 is represented by the z-axis. A generally circular or elliptical ablation path is preferably created by rotating the energy source 12 about an axis (for example, as defined by the wires W in FIG. 2). The elongate member 18, along with the housing 16 and the energy source 12, is preferably rotated, as shown in FIG. 2. Alternatively, in other configurations, the energy source 12 is rotated within the housing 16. For example, as shown in FIG. 2, the housing 16 points towards the wall tissue 2174 of an atrium. The energy source 12 in the housing 16 emits an energy beam to establish an ablation window 2172. As the housing 16 (and an elongate member 18, described below) are rotated (as shown by arrow 2124 in FIG. 2), the ablation window 2172 sweeps a generally circular ablation path 2176 creating a section of a conical shell. Further, in this example, it may be desirable to move the elongate member forwards or backwards along the Z-axis to adjust for possible variations in the anatomy. Although the ablation path is preferably linear or circular, any suitable ablation path may be created by any suitable combination of movement in the X, Y, and Z axes and rotational movement.

As shown in FIG. 1, the energy delivery system 10 of the preferred embodiments may also include an elongate member 18, coupled to the energy source 12. The elongate member 18 is preferably a catheter made of a flexible multi-lumen tube, but may alternatively be a cannula, tube or any other suitable elongate structure having one or more lumens. The elongate member 18 of the preferred embodiments functions to accommodate pull wires, fluids, gases, energy delivery structures, electrical wires, therapy catheters, navigation catheters, pacing catheters, connections and/or any other suitable device or element. As shown in FIG. 1, the elongate member 18 preferably includes a housing 16 positioned at a distal portion of the elongate member 18. The elongate member 18 further functions to move and position the energy source 12 and/or the housing 16 within a patient, such that the emitted energy beam 20 propagates into the target tissue at an appropriate angle and the energy source 12 and/or the housing 16 is moved along an ablation path such that the energy source 12 provides a partial or complete zone of ablation along the ablation path.

The energy source 12 is preferably an ultrasound transducer that emits an ultrasound beam, but may alternatively be any suitable energy source that functions to provide a source of ablation energy. Suitable sources of ablation energy include but are not limited to, radio frequency (RF) energy, microwaves, photonic energy, and thermal energy. The therapy could alternatively be achieved using cooled sources (e.g., cryogenic fluid). The energy delivery system 10 preferably includes a single energy source 12, but may alternatively include any suitable number of energy sources 12. The ultrasound transducer is preferably made of a piezoelectric material such as PZT (lead zirconate titanate) or PVDF (polyvinylidine difluoride), or any other suitable ultrasound emitting material. For simplicity, the front face of the transducer is preferably flat, but may alternatively have more complex geometry such as either concave or convex to achieve an effect of a lens or to assist in apodization—selectively decreasing the vibration of a portion or portions of the surface of the transducer—and management of the propagation of the energy beam 20. The transducer preferably has a circular geometry, but may alternatively be elliptical, polygonal, or any other suitable shape. The transducer may further include coating layers which are preferably thin layer(s) of a suitable material. Some suitable transducer coating materials may include graphite, metal-filled graphite, gold, stainless steel, magnesium, nickel-cadmium, silver, and a metal alloy. For example, as shown in FIG. 1, the front face of the energy source 12 is preferably coupled to one or more matching layers 34. The matching layer(s) preferably functions to increase the efficiency of coupling of the energy beam 20 into the surrounding fluid 28. The matching layer 34 is preferably made from a plastic such as parylene, preferably placed on the transducer face by a vapor deposition technique, but may alternatively be any suitable material, such as graphite, metal-filled graphite, metals, or ceramic, added to the transducer in any suitable manner.

Figure 3:
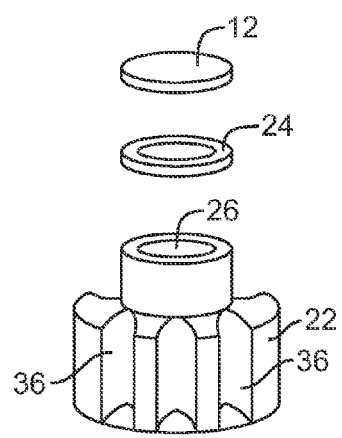
FIG. 3 illustrates an exemplary embodiment of the energy source and backing.
Figure 4A:
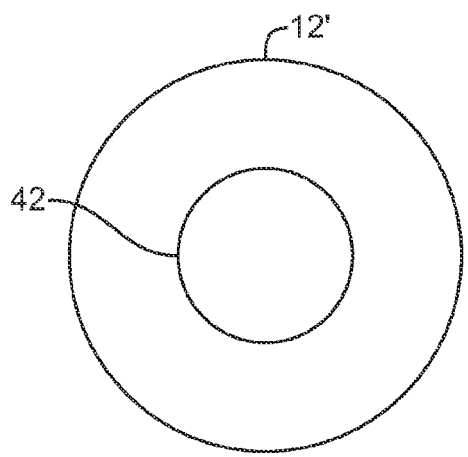
FIGS. 4A-4B illustrate alternative embodiments of an energy source.
Figure 4B:
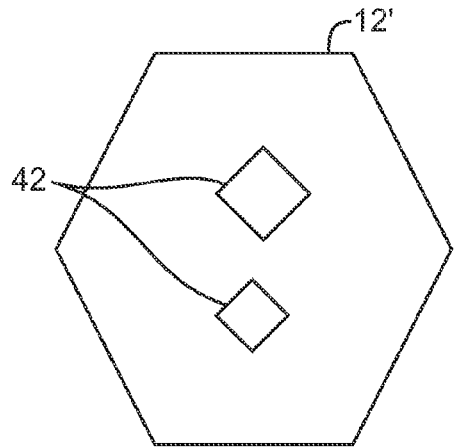

The energy source 12 is preferably one of several variations. In a first variation, as shown in FIG. 3, the energy source 12 is a disc with a flat front surface coupled to a backing 22 with an adhesive ring 24. The backing 22 forms a pocket 26 to help reflect energy in a desired direction, often distally away from the housing 16 into the treatment tissue. A plurality of axial channel or grooves 36 along the backing allow fluid to flow therepast in order to help cool the transducer 12 and prevent direct tissue contact. In a second variation, as shown in FIGS. 4A and 4B, the energy source 12' includes an inactive portion 42. In this variation, the inactive portion 42 does not emit an energy beam when the energy source 12 is energized, or may alternatively emit an energy beam with a very low (substantially zero) energy. The inactive portion 42 preferably functions to aid in the temperature regulation of the energy source, i.e. preventing the energy source from becoming too hot. In a full disk transducer, as shown in FIG. 3, the center portion of the transducer generally becomes the hottest portion of the transducer while energized. By removing the center portion or a portion of the center portion of the transducer, the energy emitted from the transducer is preferably distributed differently across the transducer, and the heat of the transducer is preferably more easily dissipated.

The inactive portion 42 is preferably a hole or gap defined by the energy source 12'. In this variation, a coolant source may be coupled to, or in the case of a coolant fluid, it may flow through the hole or gap defined by the energy source 12' to further cool and regulate the temperature of the energy source 12'. The inactive portion 42 may alternatively be made of a material with different material properties from that of the energy source 12'. For example, the material is preferably a metal, such as copper, which functions to draw or conduct heat away from the energy source 12. Alternatively, the inactive portion is made from the same material as the energy source 12, but with the electrode plating removed or disconnected from the electrical attachments 14 and or the generator. The inactive portion 42 is preferably disposed along the full thickness of the energy source 12', but may alternatively be a layer of material on or within the energy source 12' that has a thickness less than the full thickness of the energy source 12'. As shown in FIG. 4A, the energy source 12' is preferably a doughnut-shaped transducer. As shown, the transducer preferably defines a hole (or inactive portion 42) in the center portion of the transducer. The energy source 12' of this variation preferably has a circular geometry, but may alternatively be elliptical, polygonal as shown in FIG. 4B, or any other suitable shape. The energy source 12' preferably includes a singular, circular inactive portion 42, but may alternatively include any suitable number of inactive portions 42 of any suitable geometry, as shown in FIG. 4B. The total energy emitted from the energy source 12 is related to the surface area of the energy source 12 that is active (i.e. emits energy beam 20). Therefore, the size and location of inactive portion(s) 42 preferably sufficiently reduce the heat build-up in the energy source 12, while allowing the energy source 12 to provide as much output energy as possible or as desired.

Figure 5:
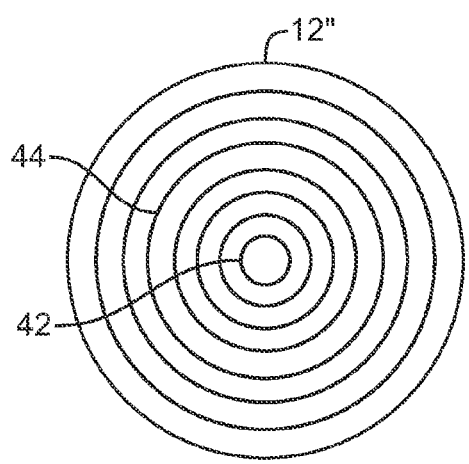
FIGS. 5-6 illustrate still other embodiments of an energy source.

In a third variation, as shown in FIG. 5, the energy source 12" preferably includes a plurality of annular transducers 44. The plurality of annular transducers is preferably a plurality concentric rings, but may alternatively have any suitable configuration with any suitable geometry, such as elliptical or polygonal. The energy source 12" may further include an inactive portion 42, such as the center portion of the energy source 12" as shown in FIG. 5. The plurality of annular transducers 44 preferably includes at least a first annular transducer and a second annular transducer. The first annular transducer preferably has material properties that differ from those of the second annular transducer, such that the first annular transducer emits a first energy beam that is different from the second energy beam emitted from the second annular ring. Furthermore, the first annular transducer may be energized with a different frequency, voltage, duty cycle, power, and/or for a different length of time from the second annular transducer. Alternatively the first annular ring may be operated in a different mode from the second annular ring. For example, the first annular ring may be run in a therapy mode, such as ablate mode which delivers a pulse of ultrasound sufficient for heating of the tissue, while the second annular ring may be run in a diagnostic mode, such as A-mode, which delivers a pulse of ultrasound of short duration, which is generally not sufficient for heating of the tissue but functions to detect characteristics of the target tissue and/or environment in and around the energy delivery system. The first annular transducer may further include a separate electrical attachment 14 from that of the second annular transducer.

Figure 6:
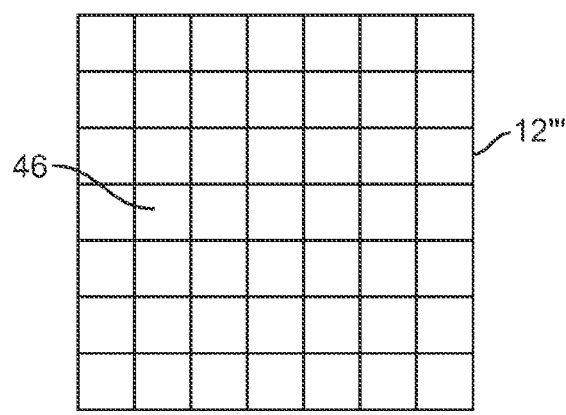

In a fourth variation, as shown in FIG. 6, the energy source 12''' preferably includes a grid of transducer portions 46. The grid of transducer portions 46 preferably has any suitable geometry such as circular, rectangular (as shown in FIG. 6), elliptical, polygonal, or any other suitable geometry. The energy source 12''' in this variation may further include a transducer portion that is inactive, such as an inactive portion as described in the second variation of the energy source 12'. The grid of transducer portions 46 preferably includes at least a first transducer portion and a second transducer portion. In a first version, the first transducer portion and the second transducer portion are preferably portions of a single transducer with a single set of material properties. The first transducer portion is preferably energized with a different frequency, voltage, duty cycle, power, and/or for a different length of time from the second transducer portion. Furthermore the first transducer portion may be operated in a different mode from the second transducer portion. For example, the first transducer portion may operate in a therapy mode, such as ablate mode, while the second transducer portion may operate in a diagnostic mode, such as A-mode. In this version, the first transducer portion may further include a separate electrical attachment 14 from that of the second transducer portion. For example, the first transducer portion may be located towards the center of the energy source 12''' and the second transducer portion may be located towards the outer portion of the energy source 12''' and the second transducer portion may be energized while the first transducer portion remains inactive. In a second version, the first transducer portion preferably has material properties that differ from those of the second transducer portion, such that the first transducer portion emits a first energy beam that is different from the second energy beam emitted from the second portion. In this version, the first transducer portion may also be energized with a different frequency, voltage, duty cycle, power, and/or for a different length of time from the second transducer portion.

2. The Electrical Attachment. As shown in FIG. 1, the electrical attachment 14 of the preferred embodiments functions to energize the energy source 12 such that it emits an energy beam 20. In use, as the energy source 12 is energized, it emits an energy beam 20 towards targeted tissue. As the energy is transferred from the energy beam 20 into the tissue, the targeted tissue portion is preferably heated sufficiently to achieve ablation. As shown in FIG. 1, the electrical attachment 14 is preferably coupled to the energy source 12. The energy delivery system 10 preferably includes two electrical attachments 14 and 14', but may alternatively include any suitable number of electrical attachments to energize the energy source 12. The energy source 12 preferably has a first electrical attachment 14 coupled the front surface of the energy source 12 which is coupled to a suitably insulated wire 38. The electrical attachment 14 is preferably accomplished by standard bonding techniques such as soldering, wire bonding, conductive epoxy, or swaging. The electrical attachment 14 is preferably placed closer to the edge of the energy source 12 so as not to disturb the energy beam 20 emitted by the energy source 12 upon being electrically energized. The energy source 12 preferably has a second electrical attachment 14' coupled the back surface of the energy source 12 which is coupled to a suitably insulated wire 38'. Wires 38 and 38' together form a pair 38", which are preferably a twisted shielded pair, a miniature coaxial cable, a metal tube braid, or are coupled in any other suitable method. The electrical attachment(s) 14 may alternatively be coupled to the energy source 12 in any other suitable fashion in any other suitable configuration.

The energy delivery system 10 of the preferred embodiments also includes an electrical generator (not shown) that functions to provide power to the energy source 12 via the electrical attachment(s) 14. The energy source 12 is preferably coupled to the electrical generator by means of the suitably insulated wires 38 and 38' connected to the electrical attachments 14 and 14' coupled to the two faces of the energy source 12. When energized by the generator the energy source 12 emits energy. The generator provides an appropriate signal to the energy source 12 to create the desired energy beam 20. The frequency is preferably in the range of 5 to 25 MHz, more preferably in the range of 8 to 20 MHz, and even more preferably in the range of 2 to 15 MHz. The energy of the energy beam 20 is determined by the excitation voltage applied to the energy source 12, the duty cycle, and the total time the voltage is applied. The voltage is preferably in the range of 5 to 200 volts peak-to-peak. In addition, a variable duty cycle is preferably used to control the average power delivered to the energy source 12. The duty cycle preferably ranges from 0% to 100%, with a repetition frequency that is preferably faster than the time constant of thermal conduction in the tissue. One such appropriate repetition frequency is approximately 40 kHz.

Figure 7:
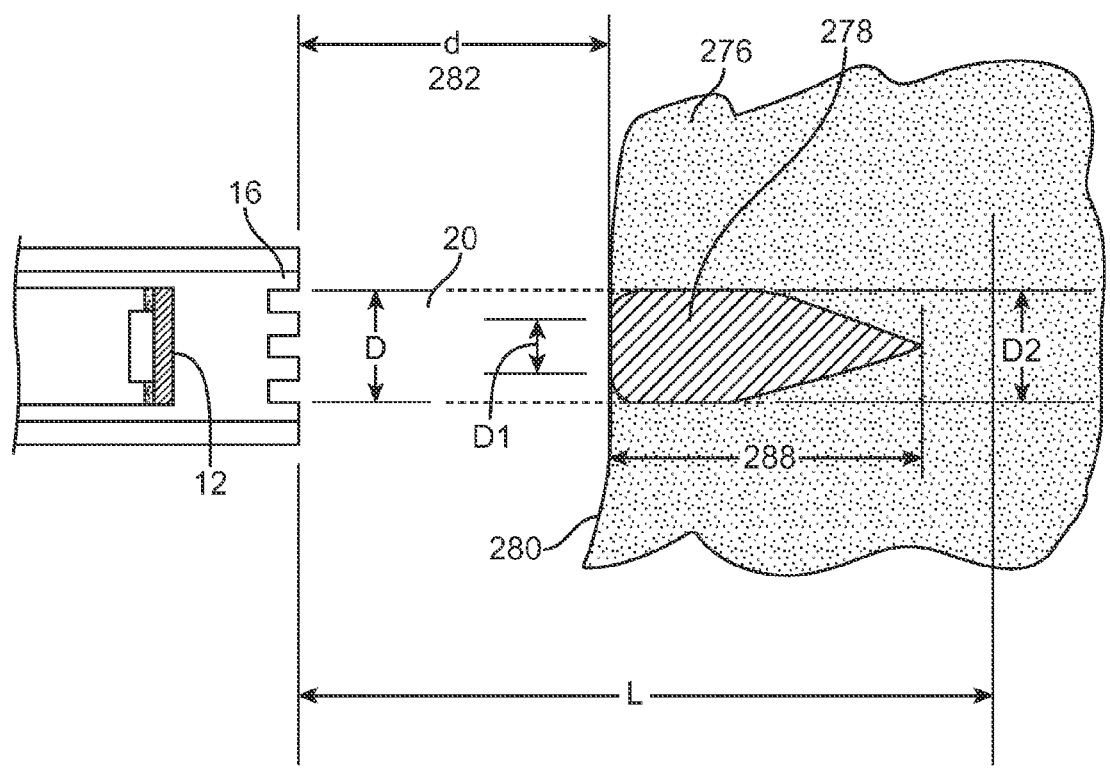
FIGS. 7-10 illustrate the energy beam and zone of ablation in tissue.

3. Energy Beam and Tissue Interaction. When energized with an electrical signal or pulse train by the electrical attachment 14 and/or 14', the energy source 12 emits an energy beam 20 (such as a sound pressure wave). The properties of the energy beam 20 are determined by the characteristics of the energy source 12, the matching layer 34, the backing 22 (described below), the electrical signal from electrical attachment 14. These elements determine the frequency, bandwidth, and amplitude of the energy beam 20 (such as a sound wave) propagated into the tissue. As shown in FIG. 7, the energy source 12 emits energy beam 20 such that it interacts with tissue 276 and forms a lesion (zone of ablation 278). The energy beam 20 is preferably an ultrasound beam. The tissue 276 is preferably presented to the energy beam 20 within the collimated length L. The front surface 280 of the tissue 276 is at a distance d (282) away from the distal face of the housing 16. As the energy beam 20 travels through the tissue 276, its energy is absorbed and scattered by the tissue 276 and most of the ablation energy is converted to thermal energy. This thermal energy heats the tissue to temperatures higher than the surrounding tissue resulting in a heated zone 278. In the zone 278 where the tissue is heated, the tissue cells are preferably rendered dead due to heat. The temperatures of the tissue are preferably above the temperature where cell death occurs in the heated zone 278 and therefore, the tissue is said to be ablated. Hence, the zone 278 is preferably referenced as the ablation zone or lesion.

4. The Physical Characteristics of the Lesion. The shape of the lesion or ablation zone 278 formed by the energy beam 20 depends on the characteristics of suitable combination factors such as the energy beam 20, the energy source 12 (including the material, the geometry, the portions of the energy source 12 that are energized and/or not energized, etc.), the matching layer 34, the backing 22 (described below), the electrical signal from electrical attachment 14 (including the frequency, the voltage, the duty cycle, the length and shape of the signal, etc.), and the characteristics of target tissue that the beam 20 propagates into and the length of contact or dwell time. The characteristics of the target tissue include the thermal transfer properties and the ultrasound absorption, attenuation, and backscatter properties of the target tissue and surrounding tissue.

The shape of the lesion or ablation zone 278 formed by the energy beam 20 is preferably one of several variations due to the energy source 12 (including the material, the geometry, the portions of the energy source 12 that are energized and/or not energized, etc.). In a first variation of the ablation zone 278, as shown in FIG. 7, the energy source 12 is a full disk transducer and the ablation zone 278 is a tear-shaped lesion. The diameter D1 of the zone 278 is smaller than the diameter D of the beam 20 at the tissue surface 280 and further, the outer layer(s) of tissue 276 preferably remain substantially undamaged. This is due to the thermal cooling provided by the surrounding fluid (cooling fluid and/or blood), which is flowing past the tissue surface 280. More or less of the outer layers of tissue 276 may be spared or may remain substantially undamaged due to the amount that the tissue surface 280 is cooled and/or the characteristics of the energy delivery system 10 (including the energy source 12 and the energy beam 20). The energy deposited in the ablation zone 278 preferably interacts with the non-surface layer(s) of tissue such that the endocardial surface remains pristine (and/or not charred). As the energy beam 20 travels deeper into the tissue, the thermal cooling is provided by the surrounding tissue, which is not as efficient as that on the surface. The result is that the ablation zone 278 has a larger diameter D2 than D1 as determined by the heat transfer characteristics of the surrounding tissue as well as the continued input of the energy from the beam 20. As the beam 20 is presented to the tissue for an extended period of time, the ablation zone 278 extends into the tissue, but not indefinitely. There is a natural limit of the depth 288 of the ablation zone 278 as determined by the factors such as the attenuation and absorption of the ultrasound energy as the energy beam 20 propagates into the tissue, heat transfer provided by the healthy surrounding tissue, and the divergence of the beam beyond the collimated length L. During this ultrasound-tissue interaction, the ultrasound energy is being absorbed by the tissue, and therefore less and less of it is available to travel further into the tissue. Thus a correspondingly smaller diameter heated zone is developed in the tissue, and the overall result is the formation of the heated ablation zone 278, which is in the shape of an elongated tear limited to a depth 288 into the tissue.

Figure 9:
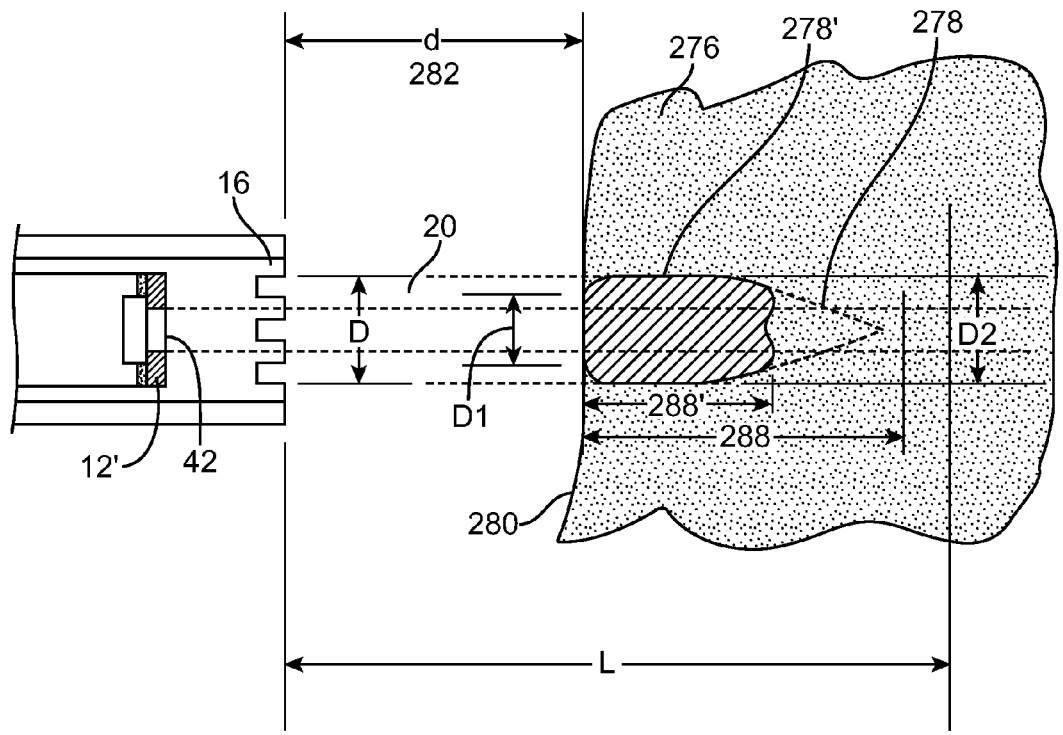

In a second variation, as shown in FIG. 9, the ablation zone 278' has a shorter depth 288'. In this variation, the lesion preferably has a more blunt shape than ablation zone 278 (FIG. 7). One possible lesion geometry of this second variation may be a tooth shaped geometry, as shown in FIG. 9, but may alternatively have any suitable shape such as a blunt tear shape, a circular shape, or an elliptical shape. As shown in FIG. 9, zone 278' (similarly to zone 278 in FIG. 7) has a diameter D1 of the zone 278' smaller than the diameter D of the beam 20 at the tissue surface 280 due to the thermal cooling provided by the surrounding fluid flowing past the tissue surface 280. In this variation, the energy source 12' preferably has an inactive portion 42 located at the center of the energy source 12', such that energy source is a doughnut-shaped transducer which emits an energy beam 20 that is generally more diffused, with a broader, flatter profile, than the energy beam 20 of the first variation (FIG. 7). The energy beam 20 emitted from the doughnut-shaped transducer, as shown in FIG. 9, preferably has a reduced peak intensity along the midline of the energy beam (as shown in cross section by the dotted lines in FIG. 9). With this ultrasound-tissue interaction, the reduced peak intensity along the midline of the energy beam is being absorbed by the tissue, and less and less of the energy is available to travel further into the tissue, forming a blunter lesion than in the first variation.

The size and characteristics of the ablation zone also depend on the frequency and voltage applied to the energy source 12 to create the desired energy beam 20. For example, as the frequency increases, the depth of penetration of ultrasound energy into the tissue is reduced resulting in an ablation zone 278 (ref. FIG. 7) of shallower depth 288. The frequency is preferably in the range of 5 to 25 MHz, more preferably in the range from 8 to 20 MHz, and even more preferably in the range from 10 to 18 MHz. The energy of the energy beam 20 is determined by the excitation voltage applied to the energy source 12 for a transducer fabricated from PZT material, for example. The voltage is preferably in the range of 5 to 200 volts peak-to-peak. In addition, a variable duty cycle is preferably used to control the average power delivered to the energy source 12. The duty cycle preferably ranges from 0% to 100%, with a repetition frequency of approximately 40 kHz, which is preferably faster than the time constant of thermal conduction in the tissue. This results in an ablation zone 278, which is created within 1 to 5 seconds, and is of depth 288 of approximately 5 millimeters (mm), and of a maximum diameter of approximately 2.5 mm in correspondence to the diameter of the energy source 12, for an average power level preferably 0.5 to 25 watts, more preferably 2 to 10 watts, and even more preferably 2 to 7 watts.

Figure 8A:
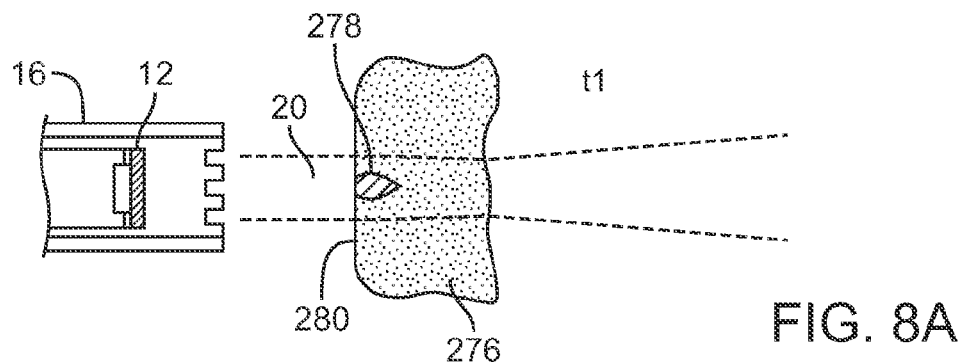
Figure 8B:
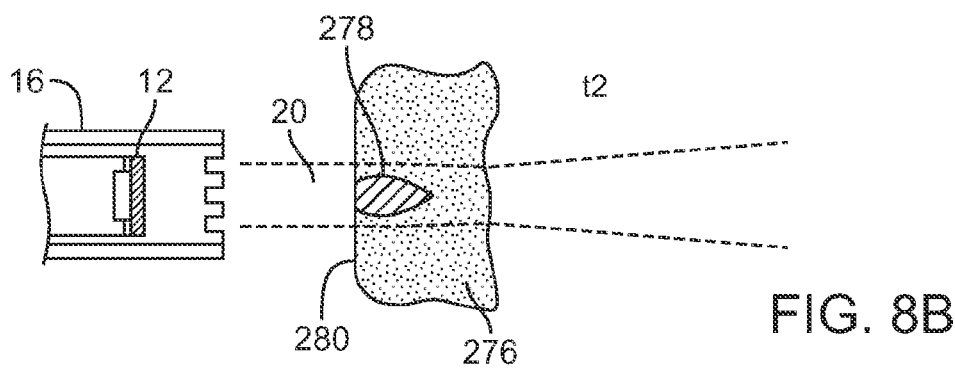
Figure 8C:
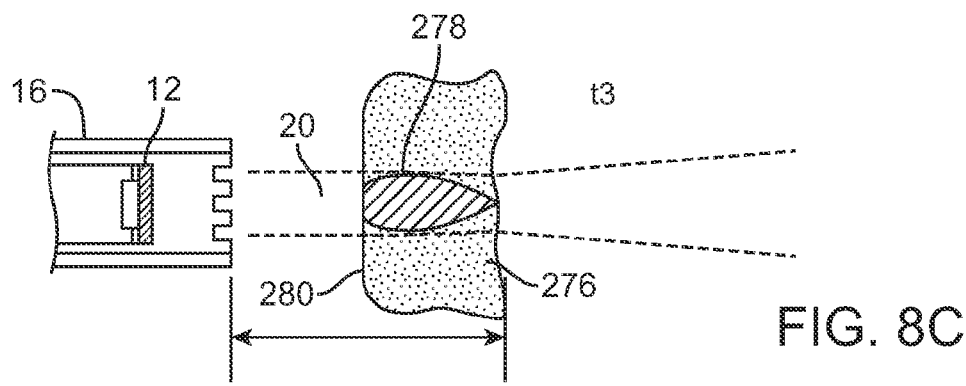
Figure 8D:
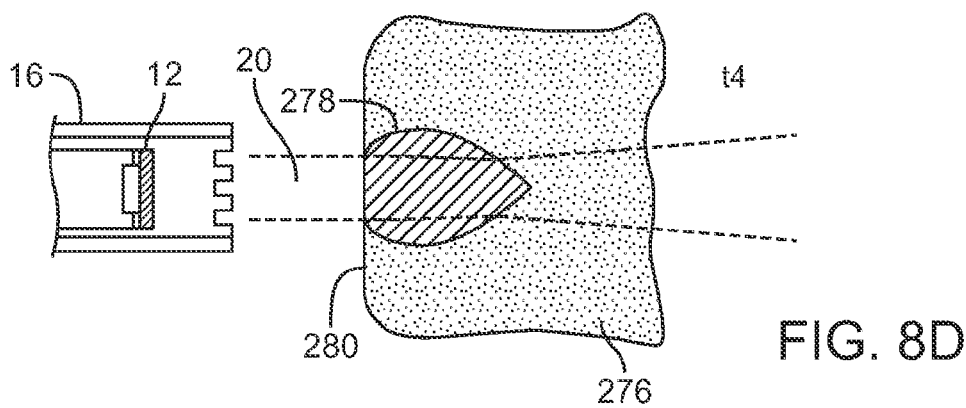

The size and characteristics of the ablation zone 278 also depend on the time the targeted tissue is contacted by the energy beam 20, as shown in FIGS. 8A-8D, which exemplify the formation of the lesion at times $t_1$, $t_2$, $t_3$ and $t_4$, respectively. The ablation zone 278 in the tissue is formed by the conversion of the ultrasound energy to thermal energy in the tissue. As the energy beam 20 initially impinges on the front surface 280 of the tissue 276 at time $t_1$, heat is created which begins to form the lesion 278 (FIG. 8A). As time passes on to $t_2$, and $t_3$ (FIGS. 8B and 8C), the ablation zone 278 continues to grow in diameter and depth. This time sequence from $t_1$ to $t_3$ preferably takes as little as 1 to 5 seconds, depending on the ultrasound energy density. As the incidence of the ultrasound beam is continued beyond time $t_3$, the ablation lesion 278 grows slightly in diameter and length, and then stops growing due to the steady state achieved in the energy transfer from its ultrasound form to the thermal form balanced by the dissipation of the thermal energy into the surrounding tissue. The example shown in FIG. 8D shows the lesion after an exposure t4 of approximately 30 seconds to the energy beam 20. Thus the lesion reaches a natural limit in size and does not grow indefinitely.

The ultrasound energy density preferably determines the speed at which the ablation occurs. The acoustic power delivered by the energy source 12 divided by the cross sectional area of the beam 20 determines the energy density per unit time. Effective acoustic power preferably ranges from 0.5 to 25 watts, more preferably from 2 to 10 watts, and even more preferably from 2 to 7 watts, and the corresponding power densities preferably range from 50 watts/cm$^2$ to 2500 watts/cm$^2$. These power densities are developed in the ablation zone. As the beam diverges beyond the ablation zone, the power density falls such that ablation will not occur, regardless of the time exposure.

Although the shape of the ablation zone 278 is preferably one of several variations, the shape of the ablation zone 278 may be any suitable shape and may be altered in any suitable fashion due to any suitable combination of the energy beam 20, the energy source 12 (including the material, the geometry, etc.), the matching layer 34, the backing 22 (described below), the electrical signal from electrical attachment 14 (including the frequency, the voltage, the duty cycle, the length of the pulse, etc.), and the target tissue the beam 20 propagates into and the length of contact or dwell time.

5. The Sensor. The energy delivery system 10 of the preferred embodiments also includes a sensor separate from the energy source and/or the energy source 12 may further function as a sensor to detect the gap (the distance of the tissue surface from the energy source 12), the thickness of the tissue targeted for ablation, the characteristics of the ablated tissue, the incident beam angle, and any other suitable parameter or characteristic of the tissue and/or the environment around the energy delivery system 10, such as the temperature. By detecting the information, the sensor (coupled to the processor, as described below) preferably functions to guide the therapy provided by the ablation of the tissue.

The sensor is preferably one of several variations. In a first variation, the sensor is preferably an ultrasound transducer that functions to detect information with respect to the gap, the thickness of the tissue targeted for ablation, the characteristics of the ablated tissue, and any other suitable parameter or characteristic. The sensor preferably has a substantially identical geometry as the energy source 12 to insure that the area diagnosed by the sensor is substantially identical to the area to be treated by the energy source 12. More preferably, the sensor is the same transducer as the transducer of the energy source, wherein the energy source 12 further functions to detect information by operating in a different mode (such as A-mode, defined below).

Figure 10:
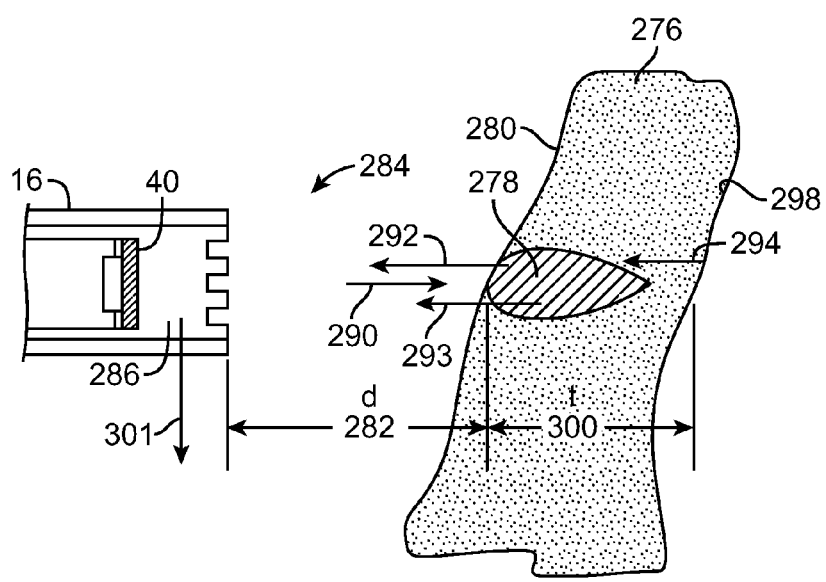

The sensor of the first variation preferably utilizes a burst of ultrasound of short duration, which is generally not sufficient for heating of the tissue. This is a simple ultrasound imaging technique, referred to in the art as A Mode, or Amplitude Mode imaging. As shown in FIG. 10, sensor 40 preferably sends a burst 290 of ultrasound towards the tissue 276. A portion of the beam is reflected and/or backscattered as 292 from the front surface 280 of the tissue 276. This returning sound wave 292 is detected by the sensor 40 a short time later and converted to an electrical signal, which is sent to the electrical receiver (not shown). The returning sound wave 292 is delayed by the amount of time it takes for the sound to travel from the sensor 40 to the front boundary 280 of the tissue 276 and back to the sensor 40. This travel time represents a delay in receiving the electrical signal from the sensor 40. Based on the speed of sound in the intervening media (fluid 286 and blood 284), information regarding the gap distance d (282) is detected. As the sound beam travels further into the tissue 276, a portion 293 of it is scattered from the lesion 278 being formed and travels towards the sensor 40. Again, the sensor 40 converts this sound energy into electrical signals and a processor (described below) converts this information into characteristics of the lesion formation such as thickness, etc. As the sound beam travels still further into the tissue 276, a portion 294 of it is reflected from the back surface 298 and travels towards the transducer. Again, the sensor 40 converts this sound energy into electrical signals and the processor converts this information into the thickness t (300) of the tissue 276 at the point of the incidence of the ultrasound burst 290. As the catheter housing 16 is traversed in a manner 301 across the tissue 276, the sensor 40 detects the gap distance d (282), lesion characteristics, and the tissue thickness t (300). The sensor preferably detects these parameters continuously, but may alternatively detect them periodically or in any other suitable fashion. This information is used to manage the delivery of continuous ablation of the tissue 276 during therapy as discussed below.

In a second variation, the sensor is a temperature sensor that functions to detect the temperature of the target tissue, the surrounding environment, the energy source 12, the coolant fluid as described below, and/or the temperature of any other suitable element or area. The temperature senor is preferably a thermocouple, but may alternatively be any suitable temperature sensor, such as a thermistor or an infrared temperature sensor. This temperature information gathered by the sensor is preferably used to manage the delivery of continuous ablation of the tissue 276 during therapy and to manage the temperature of the target tissue and/or the energy delivery system 10 as discussed below.

6. The Processor. The energy delivery system 10 of the preferred embodiments also includes a processor 33 (illustrated in FIG. 1), coupled to the sensor 40 and to the electrical attachment 14, that controls the electrical attachment 14 and/or the electrical signal delivered to the electrical attachment 14 based on the information from the sensor 40. The processor 33 is preferably a conventional processor, but may alternatively be any suitable device to perform the desired functions.

The processor 33 preferably receives information from the sensor such as information related to the gap distance, the thickness of the tissue targeted for ablation, the characteristics of the ablated tissue, and any other suitable parameter or characteristic. Based on this information, the processor preferably controls the energy beam 20 emitted from the energy source 12 by modifying the electrical signal sent to the energy source 12 via the electrical attachment 14 such as the frequency, the voltage, the duty cycle, the length of the pulse, and/or any other suitable parameter. The processor preferably also controls the energy beam 20 by controlling portions of the energy source 12 that are energized using various frequencies, voltages, duty cycles, etc. Different portions of the energy source 12 may be energized as described above with respect to the plurality of annular transducers 44 and the grid of transducer portions 46 of the energy source 12" and 12''' respectively. Additionally, the processor may further be coupled to a fluid flow controller. The processor preferably controls the fluid flow controller to increase or decrease fluid flow based on the sensor detecting characteristics of the ablated tissue, of the unablated or target tissue, the temperature of the tissue and/or energy source, and/or the characteristics of any other suitable condition.

By controlling the energy beam 20 (and/or the cooling of the targeted tissue or energy source 12), the shape of the ablation zone 278 is controlled. For example, the depth 288 of the ablation zone is preferably controlled such that a transmural lesion (a lesion through the thickness of the tissue) is achieved. Additionally, the processor preferably functions to minimize the possibility of creating a lesion beyond the targeted tissue, for example, beyond the outer atrial wall. If the sensor detects the lesion and/or the ablation window 2172 (as shown in FIG. 2) extending beyond the outer wall of the atrium or that the depth of the lesion has reached or exceeded a preset depth, the processor preferably turns off the generator and/or ceases to send electrical signals to the electrical attachment(s) 14.

Additionally, the processor preferably functions to maintain a preferred gap distance between the energy source and the tissue to be treated. The gap distance is preferably between 0 mm and 30 mm, more preferably between 1 mm and 20 mm. If the sensor detects the lesion and/or the ablation window 2172 (as shown in FIG. 2) extending beyond the outer wall of the atrium or if it does not reach the outer wall of the atrium, or that the depth of the lesion has either not reached or has exceeded a preset depth, the processor preferably repositions the energy delivery system. For example, as the housing 16 (and an elongate member 18, described below) are rotated (as shown by arrow 2124 in FIG. 2), the ablation window 2172 preferably sweeps a generally circular ablation path 2176 creating a section of a conical shell. However, if the sensor determines that the ablation window 2172 is not reaching the wall of the atrium, the processor preferably moves the elongate member forwards or backwards along the Z-axis, or indicates that it should be moved, to adjust for the possible variations in the anatomy. In this example, the operator can reposition the elongate member, or the processor is preferably coupled to a motor drive unit or other control unit that functions to position the elongate member 18.

Figure 11:
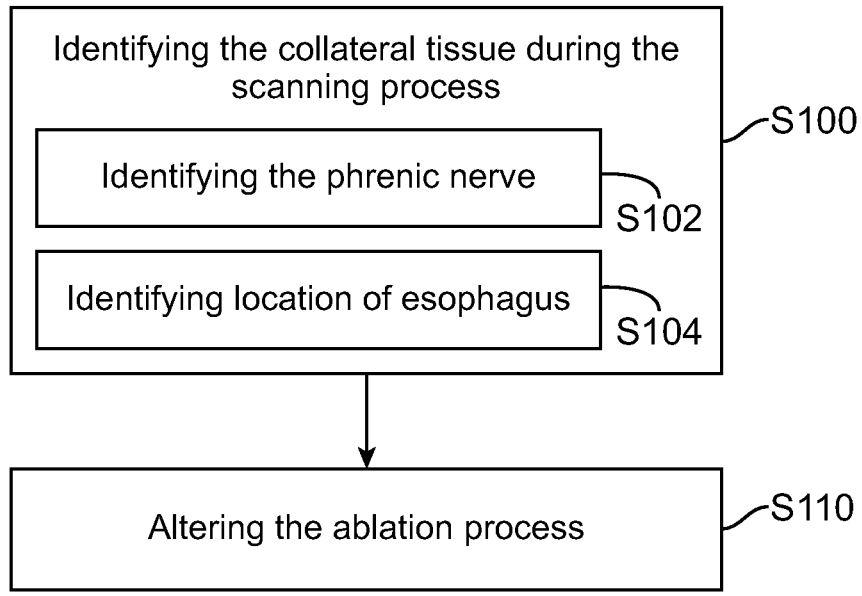
FIG. 11 shows a flowchart of an exemplary method of collateral tissue compensation.

7. Method of Collateral Tissue Compensation. As shown in FIG. 11 an exemplary method of collateral tissue compensation includes identifying collateral tissue during a scanning process S100 and altering the ablation process S110.

Step S100, which recites identifying collateral tissue during a scanning process, functions to sense and detect the collateral tissue locations. Preferably, the scanning process occurs during a diagnostic sweep prior to tissue ablation. The diagnostic sweep preferably includes gathering of gap data, tissue thickness, and/or any other suitable tissue information to aid in the ablation process. The diagnostic sweep may alternatively be only composed of the scanning process for collateral tissue. Alternatively, the scanning process may be performed periodically during the ablation process. As another alternative, the scanning process may be performed during a diagnostic sweep and during the ablation process. The collateral tissue identified is preferably any tissue or anatomical structure that is sensitive to ablation, sensitive to overheating, or any other characteristic that may require special treatment during the ablation process, including, but not limited to esophageal tissue and nerves such as the phrenic nerve. The identification of the collateral tissue is preferably a specialized test adapted to identify a single collateral tissue type, or alternatively may identify multiple collateral tissue types that have shared or overlapping properties. The collateral tissue is preferably identified by comparing standardized tissue characteristics with measured tissue thickness, tissue motion, relative position, or any suitable sensible characteristic. As discussed below, Step S100 may additionally include the additional steps of identifying the phrenic nerve S102 and/or identifying location of esophagus S104.

Step S110, which recites altering the ablation process based on information previously obtained from the collateral tissue identification, functions to modify the treatment of collateral tissue during the ablation process. Preferably, the ablation path is modified to exclude collateral tissue. The ablation path may be altered so the path deviates from the original planned path and merely avoids the collateral tissue. Alternatively, the ablation path may be changed completely as in the case when the collateral tissue makes it impossible to use the originally planed ablation path. As another alternative, the energy beam may be altered to superficially ablate the tissue. This alternative functions to form a transmural lesion, but does so using a specialized technique that is customized to not damage the collateral tissue. The specialized technique may be a faster speed during ablation, lower beam energy, extra tissue sensing, or any other suitable alterations to the ablation process.

Figure 12:
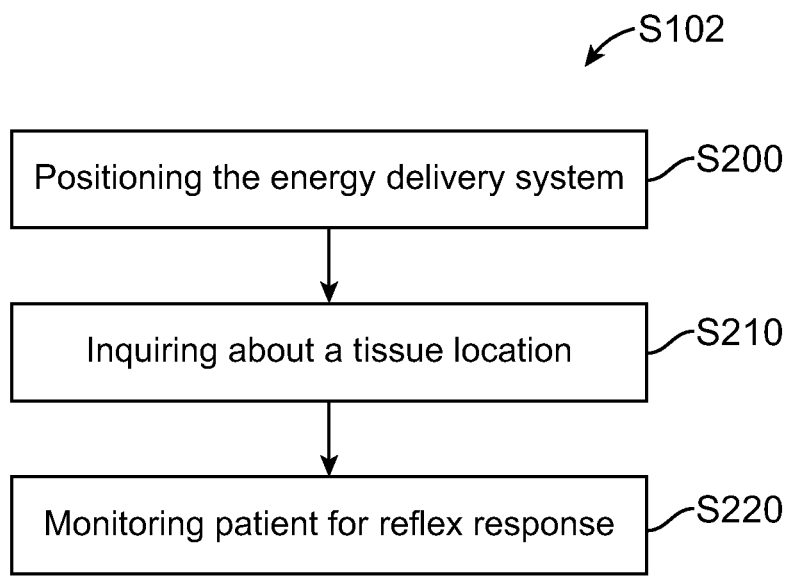
FIG. 12 shows a flowchart of an exemplary method of identifying the phrenic nerve.

As shown in FIGS. 11 and 12, Step S100 may additionally include the additional step of identifying the phrenic nerve S102. Step S102 includes positioning the energy delivery system S200, inquiring about the tissue by bumping or electrically stimulating a tissue location S210, and monitoring the patient for a reflex response S220 to the inquiry S210. The method of identifying the phrenic nerve functions to utilize the reflex response wherein a person hiccups when his phrenic nerve is physically pushed or electrically stimulated.

Step S200, which recites positioning the energy delivery system, functions to move the energy delivery system to a designated position. Preferably, the designated position is a position that is a part of a diagnostic sweep performed before the ablation sweep. Alternatively, the location of the phrenic nerve may be estimated after the diagnostic sweep (a systematic scan to acquire tissue information). The diagnostic sweep preferably generates an anatomical tissue map from which the phrenic nerve location can be estimated. The estimated location preferably reduces the number of positions through which the energy delivery system must iterate before identifying the phrenic nerve. As another alternative, the position may be the current position of ablation. The phrenic nerve is preferably identified during the ablation process in this alternative.

Step S210, which recites inquiring about a tissue location, functions to apply a mechanical force on the phrenic nerve. The mechanical force preferably incites a reflex response of a hiccup event by the patient. Preferably, the energy delivery device delivers the mechanical force as an ultrasound pulse. The ultrasound pulse is preferably a short duration high intensity signal; a resulting pressure wave then momentarily bumps or deforms the phrenic nerve. The ultrasound may, by a series of pulses, a high or low frequency signal, or any other suitable ultrasound signal, deform the phrenic nerve. Alternatively, the energy delivery system may use a rigid structure that projects outward from the device and that can be used to physically push on tissue locations such as a nerve. The rigid structure may additionally serve other purposes such as a wire to act as the axis of rotation, an elongated member providing slidable z-axis actuation, or any other suitable structure of the energy delivery system.

Inquiring step S210 about a tissue location may also be performed by electrically stimulating the tissue. Electrical stimulation of the phrenic nerve will similarly incite the reflex response of a hiccup event by the patient. An exemplary device for electrically or mechanically stimulating the phrenic nerve is discussed below with reference to FIG. 16B.

Step S220, which recites monitoring a patient for a reflex response to an inquiry such as a bump or electrical stimulation, functions to audibly monitor the patient for a hiccup when the phrenic nerve is bumped. The bumping of the phrenic nerve preferably incites an audible hiccup from the patient. A nerve signal, muscle contraction, or any other suitable internal or external reflex response may alternatively be monitored. Preferably, the physician or operator signals to the device through a button or any suitable input device when a hiccup is observed. Alternatively, an audio microphone or any suitable sensor may be used to detect the audible hiccup and electronically signal to the device when a hiccup occurs. The microphone is preferably positioned near the source of the sound such as the mouth or any other suitable position. Another alternative may use a pressure sensor to detect the contraction of the diaphragm during the hiccup. The position of the energy delivery at the time of the hiccup is preferably used to identify the location of the phrenic nerve.

Figure 16A:
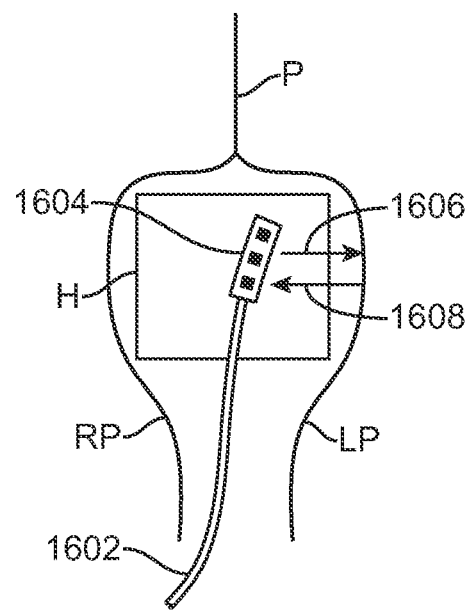
FIGS. 16A-16B illustrate location of the phrenic nerve.
Figure 16B:
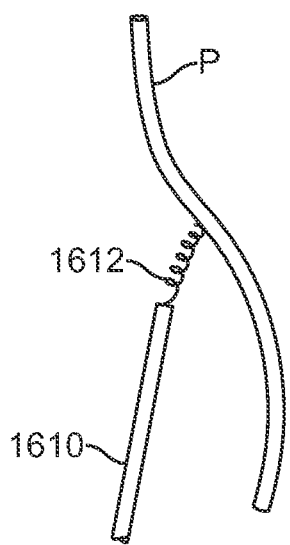

Referring now to FIG. 16A, catheter 1602 having an energy source and sensor 1604 similar to the embodiment of FIG. 1 is positioned in the heart H in order to identify location of the phrenic nerve P which typically has a left branch LP which passes over the left ventricle, and a right branch RP which passes over the right atrium. Ultrasonic or other energy 1606 is transmitted from the energy source and sensor 1604 to the nerve and then the sensor captures energy 1608 bouncing back from the nerve, thereby allowing the nerve to be located. Alternatively, energy from the energy source provides a mechanical force to the nerve and then the hiccup reflex is monitored separately. FIG. 16B illustrates an alternative embodiment where an instrument 1610 such as a catheter or other device having a flexible wire tip 1612 is used to probe and touch the nerve P causing a hiccup reflex in the patient and allowing the location of the nerve to be determined. In alternative embodiments, flexible wire tip 1612 may also be an electrode that is used to deliver an electrical signal to the phrenic nerve. The electrode may be a monopolar electrode with a return path elsewhere (e.g. a Bove plate), or the electrode may be a bipolar electrode. Wires or other electrical conductors (not shown) may run through the instrument 1610 allowing the electrode to be coupled to a power source and controlled from a proximal end of the instrument 1610, preferably outside the patient's body.

Figure 13:
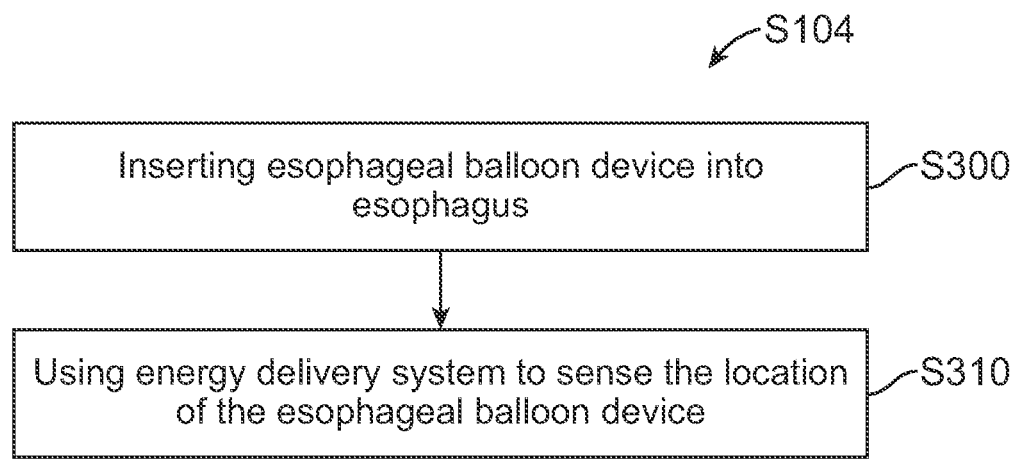
FIG. 13 shows a flowchart of an exemplary method of identifying the location of the esophagus.
Figure 14:
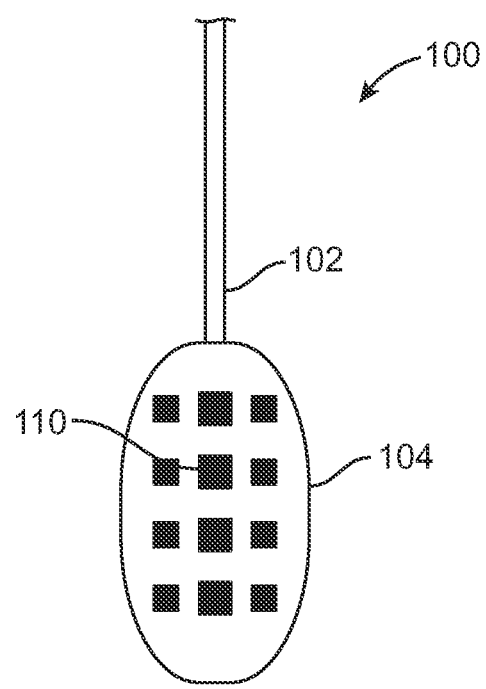
FIG. 14 illustrates an exemplary embodiment of an esophageal catheter.
Figure 15:
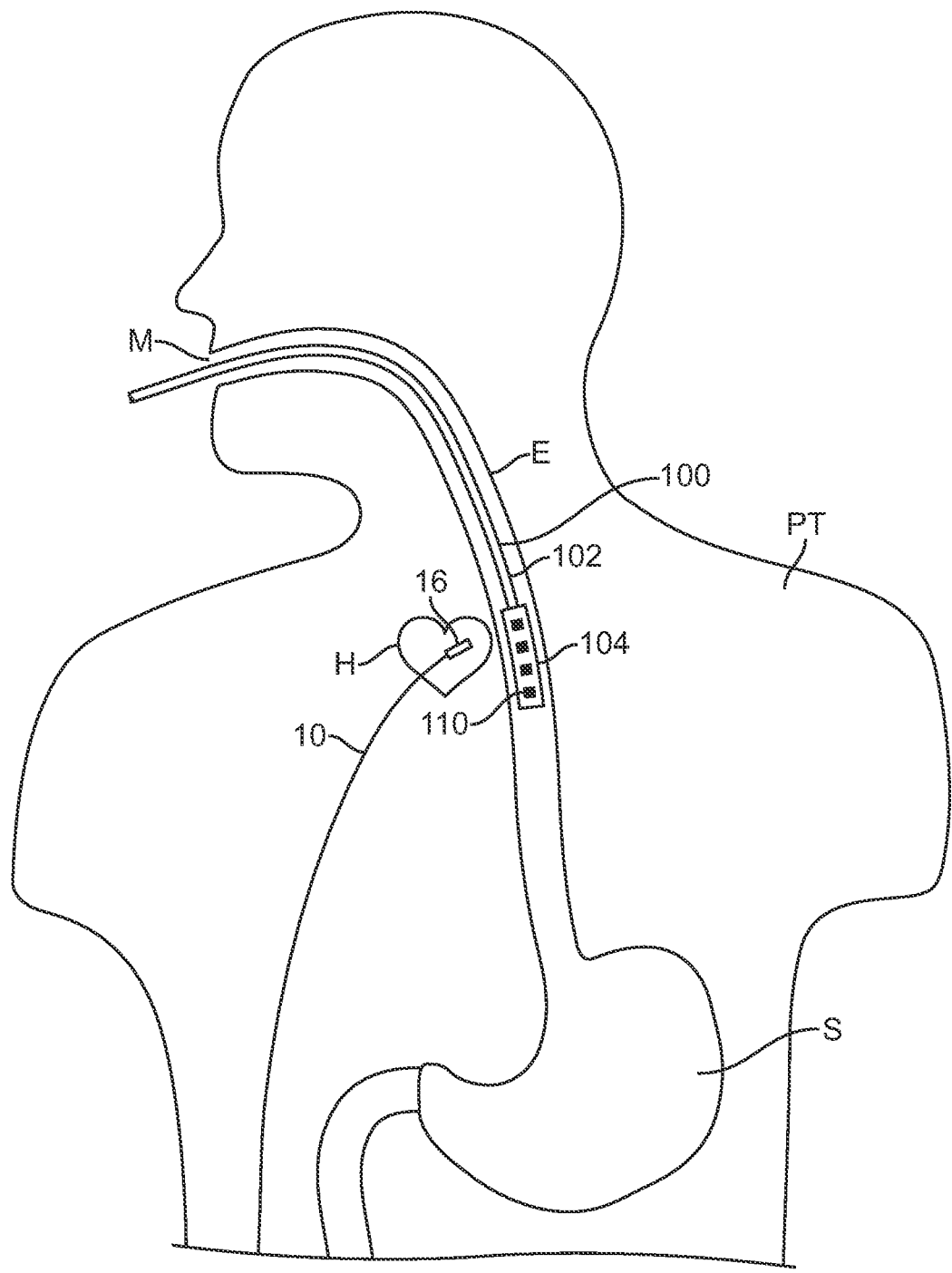
FIG. 15 illustrates insertion of a detection device in the esophagus.

Referring back to FIGS. 11 and 13, Step S100 may additionally and/or alternatively include the additional steps S104 of identifying the location of the esophagus. Step S104 includes inserting an esophageal balloon device into the esophagus S300 and using an energy delivery system to sense the location of the esophageal balloon device S310.

Step S300, which recites inserting an esophageal balloon device into the esophagus, functions to position an esophageal balloon in the esophagus to aid in the sensing of the esophagus location behind heart tissue and may further provide protection of the esophagus during ablation of the heart tissue. The esophageal balloon is preferably composed of a catheter balloon and transponder. The esophageal balloon is preferably a catheter balloon device, which is well known in the art, and additional details are provided below. The transponder functions to be an element detected through the heart and esophagus tissue. Preferably, the esophageal balloon is filled with a fluid such as saline, water, or a gas (e.g. carbon dioxide, air). Liquids such as saline or water are preferably filled with microbubbles to enhance echogenicity. water. The water is preferably sensed by the ultrasound signal of the energy delivery device and functions to be the transponder. The water may further function to cool the esophagus tissue during the ablation process. Alternatively, the transponder may be any active sensor (device sending out a signal) or passive sensor (device able to be sensed without requiring internal power source). The transponder may be a balloon material, a chemical substance, RFID tags, a string of infrared light beacons, an ultrasound transducer, or any other suitable transponder.

Step S310, which recites using an energy delivery system to sense the location of the esophageal balloon device, functions to determine the location of the esophagus behind the heart tissue. Preferably, the energy delivery system can use ultrasound sensing to detect the water within the esophageal balloon. The water preferably generates a unique ultrasound echo that can be distinguished from an echo from tissue. Alternatively, the energy delivery system may include a specialized sensor that corresponds to the type of transponder used in the esophageal balloon. The specialized sensor may be an RFID reader, an IR photodetector, a material sensor, or any other suitable sensor.

8.

While the above is a complete description of the preferred embodiments of the invention, various alternatives, modifications, and equivalents may be used. For example, additional embodiments and additional details on various aspects of an ablation system are disclosed in copending U.S. Provisional Patent Application Nos. 61/110,905; 61/115,403; 61/148,809; 61/109,973; 61/109,875; 61/109,879; 61/109,881; 61/109,882; 61/109,889; 61/109,893; 61/254,997; and U.S. patent application Ser. Nos. 11/747,862; 11/747,867; 12/480,929; 12/480,256; 12/483,174; 12/482,640; 12/505,326; 12/505,335; the entire contents of which have previously been incorporated herein by reference. Therefore, the above description should not be taken as limiting in scope of the invention which is defined by the appended claims.

What is claimed is:

1. A tissue ablation method for treating atrial fibrillation in a patient, said method comprising:
   locating an ostium of a pulmonary vein;
   positioning an interventional catheter adjacent the ostium, the interventional catheter having an energy source;
   identifying collateral tissue adjacent the ostium;
   ablating tissue around the ostium with energy from the energy source so as to form a contiguous lesion circumscribing the ostium, the lesion blocking aberrant electrical pathways in the tissue so as to reduce or eliminate the atrial fibrillation; and
   modifying the ablating so as to avoid ablating or otherwise damaging the collateral tissue, wherein modifying comprises changing the continuous lesion circumscribing the ostium to a new lesion path that continuously circumscribes the ostium.

2. The method of claim 1, wherein the interventional catheter further comprises a sensor adjacent the energy source, and wherein the locating step comprises delivering energy from the energy source toward the tissue adjacent the ostium, and sensing energy reflected from the tissue adjacent the ostium with the sensor.

3. The method of claim 2, wherein the sensor comprises at least a portion of the energy source.

4. The method of claim 1, wherein the positioning comprises intravascularly advancing the interventional catheter into a left atrium of the patient's heart.

5. The method of claim 1, wherein the identifying comprises characterizing properties of the tissue adjacent the ostium and comparing the properties with known tissue properties.

6. The method of claim 1, wherein the identifying comprises a diagnostic sweep of tissue adjacent the ostium, the sweep being a systematic scan to acquire information about the tissue adjacent the ostium.

7. The method of claim 1, wherein the identifying is performed while the ablating is being performed.

8. The method of claim 1, wherein the modifying comprises modifying the lesion so as to avoid the collateral tissue.

9. The method of claim 1, wherein the modifying comprises changing the energy emitted from the energy source so as to avoid damaging the collateral tissue.

10. The method of claim 1, wherein the collateral tissue comprises an esophagus.

11. The method of claim 10, wherein the identifying comprises positioning an esophageal detection device into the esophagus.

12. The method of claim 11, wherein the identifying comprises sensing the presence of the detection device through one or more layers of tissue.

13. The method of claim 11, wherein the esophageal detection device comprises a balloon catheter.

14. The method of claim 13, wherein the balloon catheter is filled with a fluid, the method further comprising sensing the fluid in the balloon catheter with an ultrasound signal delivered by the energy source.

15. The method of claim 14, wherein the fluid is one of saline, water, air, and carbon dioxide.

16. The method of claim 11, wherein the esophageal detection device comprises a transponder.

17. The method of claim 16, wherein the transponder comprises one of a reflective material, a chemical substance, RFID tag, a capacitive plate, an inductive component, an ultrasound transducer, and an infrared light.

18. The method of claim 11, wherein the esophageal detection device further protects the esophagus by cooling the esophagus.

19. The method of claim 11, wherein the identifying comprises sensing the esophageal detection device with the interventional catheter.

20. A tissue ablation system for treating atrial fibrillation in a patient, said system comprising:
    an interventional catheter having an energy source and a sensor, wherein the energy source is adapted to deliver a beam of energy to tissue thereby ablating tissue around an ostium of a pulmonary vein to form a contiguous lesion circumscribing the ostium, the lesion blocking aberrant electrical pathways in the tissue so as to reduce or eliminate the atrial fibrillation; and
    an esophageal detection device positionable in the esophagus, the detection device having a transponder detectable by the sensor through one or more layers of tissue, and
    wherein the sensor provides feedback to the interventional catheter based on the detection of the esophageal detection device so as to modify the continuous lesion circumscribing the ostium to a new lesion path that continuously circumscribes the ostium.

21. The system of claim 20, wherein the detection device comprises a balloon catheter.

22. The system of claim 21, wherein the balloon catheter is at least partially filled with a fluid, and wherein the beam of energy comprises an ultrasound signal that reflects off the fluid filled portion of the balloon catheter and is sensed by the sensor.

23. The system of claim 22, wherein the fluid is one of saline, water, air, and carbon dioxide.

24. The system of claim 20, wherein the transponder comprises one of a reflective material, a chemical substance, RFID tag, a capacitive plate, an inductive component, an ultrasound transducer, and an infrared light.

25. The system of claim 20, wherein the energy source comprises an ultrasound transducer.

26. The system of claim 25, wherein the sensor comprises at least a portion of the ultrasound transducer.

* * * * *